United States Patent
Nishiguchi

(10) Patent No.: US 10,546,740 B2
(45) Date of Patent: Jan. 28, 2020

(54) MASS SPECTROMETRY DEVICE AND ION DETECTION DEVICE

(71) Applicant: SHIMADZU CORPORATION, Kyoto-shi, Kyoto (JP)

(72) Inventor: Masaru Nishiguchi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 16/343,953

(22) PCT Filed: Oct. 24, 2016

(86) PCT No.: PCT/JP2016/081447
§ 371 (c)(1),
(2) Date: Apr. 22, 2019

(87) PCT Pub. No.: WO2018/078693
PCT Pub. Date: May 3, 2018

(65) Prior Publication Data
US 2019/0252178 A1    Aug. 15, 2019

(51) Int. Cl.
*H01J 49/16*    (2006.01)
*H01J 49/04*    (2006.01)
(Continued)

(52) U.S. Cl.
CPC .......... *H01J 49/167* (2013.01); *G01N 27/622* (2013.01); *H01J 49/0445* (2013.01);
(Continued)

(58) Field of Classification Search
USPC ........................................................ 250/288
See application file for complete search history.

(56) References Cited

U.S. PATENT DOCUMENTS

| 5,412,208 A | 5/1995 | Covey et al. |
| 6,410,914 B1 * | 6/2002 | Park ...................... H01J 49/107 250/282 |

(Continued)

FOREIGN PATENT DOCUMENTS

| CN | 1959401 A | 5/2007 |
| EP | 1 739 720 A2 | 1/2007 |

(Continued)

OTHER PUBLICATIONS

Ching Wu et al., "Separation of Isomeric Peptides Using Electrospray Ionization/High-Resolution Ion Mobility Spectrometry," Anal. Chem., Jan. 15, 2000, pp. 391-395, vol. 72, No. 2.

(Continued)

*Primary Examiner* — Kiet T Nguyen
(74) *Attorney, Agent, or Firm* — Sughrue Mion, PLLC

(57) ABSTRACT

A focusing electrode (8) of a flat plate shape is arranged so that an inlet end (9a) of a heated capillary (9) for introducing ions into a vacuum chamber as a subsequent stage is inserted into an opening portion (8a) of the focusing electrode (8). A reflecting electrode (7) of a flat plate shape is arranged at a position opposing the focusing electrode (8) across a spray flow ejected from an ionization probe (5). An auxiliary electrode (6) is grounded and arranged between the ionization probe (5) and each of the reflecting electrode (7) and the focusing electrode (8). The heated capillary (9) is grounded, and during a measurement of positive ions, a voltage V1 and a voltage V2, both satisfying a relationship of V1>V2>0, are respectively applied to the reflecting electrode (7) and the focusing electrode (8). A reflecting electric field for reflecting and deflecting ions generated from sample components and carried by the spray flow is created within a space between the reflecting electrode (7) and the focusing electrode (8), and a focusing electric field for focusing ions to the inlet end (9a) is created in an area near the inlet end (9a).

(Continued)

The ions generated from sample components are separated from a gas stream and efficiently collected into the inlet end (9a), to be drawn into the heated capillary (9) and sent to a mass spectrometry section.

7 Claims, 4 Drawing Sheets

(51) Int. Cl.
  *G01N 27/62* (2006.01)
  *H01J 49/06* (2006.01)
  *H01J 49/42* (2006.01)
(52) U.S. Cl.
  CPC .......... *H01J 49/062* (2013.01); *H01J 49/068* (2013.01); *H01J 49/4215* (2013.01)

(56) References Cited

U.S. PATENT DOCUMENTS

| | | | | |
|---|---|---|---|---|
| 7,204,431 B2 * | 4/2007 | Li | ................. | H01J 49/167 239/3 |
| 2002/0179832 A1 * | 12/2002 | Fischer | .............. | G01N 30/7253 250/288 |
| 2005/0072934 A1 | 4/2005 | Frazer et al. | | |
| 2007/0023675 A1 | 2/2007 | Fischer et al. | | |
| 2009/0250608 A1 | 10/2009 | Mordehai et al. | | |
| 2010/0148060 A1 | 6/2010 | Panayi | | |
| 2018/0011057 A1 | 1/2018 | Nishiguchi | | |

FOREIGN PATENT DOCUMENTS

| WO | 2009/124298 A2 | 10/2009 |
|---|---|---|
| WO | 2016/117066 A1 | 7/2016 |

OTHER PUBLICATIONS

International Search Report for PCT/JP2016/081447 dated Jan. 10, 2017 (PCT/ISA/210).
Written Opinion of the International Searching Authority for PCT/JP2016/081447 dated Jan. 10, 2017 (PCT/ISA/237).
Communication dated Dec. 19, 2017 from the European Patent Office in counterpart application No. 15878760.6.
Communication dated Jun. 1, 2018, issued by the State Intellectual Property Office of People's Republic of China in counterpart application No. 201580074229.2.
International Search Report of PCT/JP2015/051622 dated Mar. 31, 2015.

* cited by examiner

ION TRAJECTORY

EQUIPOTENTIAL LINE

REFERENCE MASS SPECTRUM

INCREASED RATIO OF PEAK SIGNAL INTENSITY

MASS SPECTROMETRY DEVICE AND ION DETECTION DEVICE

CROSS REFERENCE TO RELATED APPLICATIONS

This application is a National Stage of International Application No. PCT/JP2016/081447 filed Oct. 24, 2016.

TECHNICAL FIELD

The present invention relates to a mass spectrometer and ion detection device, and more specifically, to a mass spectrometer and ion detection device having an ion source for ionizing a component in a liquid sample by spraying the sample into an ambience of substantially atmospheric pressure.

BACKGROUND ART

In a liquid chromatograph mass spectrometer (LC-MS) in which a mass spectrometer is used as the detector for a liquid chromatograph (LC), an ion source which employs an atmospheric pressure ionization method, such as electrospray ionization (ESI), atmospheric pressure chemical ionization (APCI) or atmospheric pressure photoionization (APPI), is used to ionize a compound in a liquid sample. In a mass spectrometer employing such an atmospheric pressure ion source, ions generated within an ionization chamber in which an ambience of substantially atmospheric pressure is present need to be introduced into a vacuum chamber in which a vacuum atmosphere is maintained. To improve the sensitivity of the analysis, it is particularly important to increase the amount of ions generated within the ionization chamber, and to improve the efficiency of introducing ions from the ionization chamber into the vacuum chamber.

A commonly known technique aimed at increasing the amount of ions generated within an ESI ion source, which is a typically used atmospheric pressure ion source, is to supply a stream of heated gas onto electrically charged droplets sprayed from an ionization probe to promote desolvation of those droplets. For example, in a device described in Patent Literature 1, a stream of heated gas is supplied so as to intersect a traveling direction of the electrically charged droplets sprayed from the ionization probe. In another device, described in Patent Literature 2, a stream of heated gas is ejected in a hollow cylindrical form coaxially with the spray flow of the electrically charged droplets ejected from the ionization probe, i.e., the flowing direction of the heated gas is the same as the traveling direction of the electrically charged droplets. Both of these configurations have been proven to be effective for increasing the amount of ions to be generated. At the moment, desolvation techniques using heated gas based on one of the two aforementioned systems are adopted in almost all commercially offered mass spectrometers equipped with atmospheric pressure ion sources.

In an atmospheric pressure ion source, the arrangement of the ionization probe and an ion introduction section (e.g., ion introduction tube or sampling cone) is normally determined so that the spraying direction of the droplets from the ionization probe extends orthogonally or obliquely to the direction of introducing ions into the vacuum chamber, in order to prevent large droplets among the sample droplets sprayed from the ionization probe from being introduced into the vacuum chamber. The ions generated from the sample droplets are drawn into the ion introduction section and carried into the vacuum chamber by a gas stream flowing from the ionization chamber into the ion introduction section mainly due to the differential pressure between the two ends of the ion introduction section.

The direction of the aforementioned heated gas ejected for promoting the desolvation is normally different from that of the gas stream flowing into the ion introduction section produced by the differential pressure. Therefore, the stream of heated gas has no effect of increasing the amount of gas stream flowing into the ion introduction section. In the case of the configuration described in Patent Literature 2, the stream of heated gas may be a gas stream which is orthogonal to the ion introduction direction in an area near the ion introduction port, i.e., a gas stream which flows in a direction which interferes with the introduction of the ions. Although the heated gas is effective for increasing the amount of ion generation, it cannot be considered to be effective from the viewpoint of improving the efficiency of introducing ions from the ionization chamber into the vacuum chamber.

One method for improving the ion introduction efficiency is proposed in Patent Literature 2, in which a voltage applied to the ion introduction port is adjusted to create an appropriate electric field in the vicinity of the ion introduction port so that the ions near the ion introduction port will be attracted and collected into the same port by the effect of the electric field. However, it is difficult to create an electric field which is strong enough to sufficiently collect the ions against the powerful stream of heated gas flowing in the orthogonal direction to the ion introduction direction. Accordingly, in such a method, it is difficult to significantly improve the efficiency of introducing the ions from the ionization chamber into the vacuum chamber.

In view of such a problem, the applicant proposes a novel configuration of an atmospheric pressure ion source as described in in Patent Literature 3. In a mass spectrometer described in Patent Literature 3, an auxiliary electrode having a cylindrical shape and a reflecting electrode also having a cylindrical shape are arranged anterior to a spray flow ejected from an ionization probe and concentrically about the central axis of the spray flow. The auxiliary electrode and the reflecting electrode are coaxially arranged with a predetermined space from each other, and an ion introduction port is arranged within a space between these two electrodes. The auxiliary electrode and an ion introduction section are grounded, while the reflecting electrode is supplied with a predetermined direct-current voltage having the same polarity as measurement target ions. As a result, a reflecting electric field which reflects ions and electrically charged droplets originating from sample components, being carried by the spray flow, is created within the space between the auxiliary electrode and the reflecting electrode, and a focusing electric field for focusing ions to the ion introduction port is also created in an area near the ion introduction port. Due to the effect of these electric fields, the ions originating from the sample components are separated from the gas flow in the spray flow and gathered around the ion introduction port, to be efficiently drawn into the ion introduction section.

CITATION LIST

Patent Literature

Patent Literature 1: U.S. Pat. No. 5,412,208 A
Patent Literature 2: WO 2009/124298 A
Patent Literature 3: WO 2016/117066 A Non Patent Literature Non Patent Literature 1: Ching Wu and three others authors, "Separation of Isomeric Peptides Using Electrospray Ionization/High-Resolution Ion Mobility Spectrometry", Anal. Chem., 2000, Vol. 72, pp. 391-395

SUMMARY OF INVENTION

Technical Problem

According to the configuration described in Patent Literature 3, it is possible to improve the ion collection efficiency as compared with earlier ion source configurations. However, for example, when the flow rate of the liquid sample is high, or when a nebulized gas stream is used for spraying the liquid sample, an increased force of the spray flow tends to make it difficult to improve the efficiency of collecting ions. This is presumably because the ions are pushed by the forceful spray flow and are thus less likely to reach the ion introduction port, even though the ions are separated from the gas stream by the reflecting electric field.

The present invention has been developed to solve the aforementioned problem. Its primary objective is to provide a mass spectrometer and ion detection device capable of, particularly even when a spray flow ejected from an ionization probe is powerful, efficiently collecting and sending ions generated within the spray flow and electrically charged droplets to subsequent stages for ion detection, with minimum waste of the ions and the electrically charged droplets.

Solution to Problem

The mass spectrometer according to the present invention developed for solving the previously described problem is a mass spectrometer provided with: an ion source including an ionization probe for spraying a liquid sample into an ionization chamber in which an ambience of atmospheric pressure is present; and an ion introduction section for sending, from the ionization chamber to a vacuum chamber, ions generated by the ion source from a component contained in sample droplets sprayed from the ionization probe, where the arrangement of the ionization probe and the ion introduction section is determined so that the spraying direction of the liquid sample from the ionization probe extends orthogonally or obliquely to the direction of introducing the ions from the ionization chamber by the ion introduction section, the mass spectrometer including:

a) a focusing electrode arranged to surround an inlet port of the ion introduction section, without being in contact with the ion introduction section;

b) a reflecting electrode arranged at a position opposing the inlet port of the ion introduction section and the focusing electrode across the spray flow of sample droplets ejected from the ionization probe;

c) an auxiliary electrode for shielding an electric field, the auxiliary electrode being arranged between the ionization probe and each of the reflecting electrode and the focusing electrode, the auxiliary electrode having an opening portion through which the droplets sprayed from the ionization probe and ions generated from the droplets are passable; and d) a voltage supplier for applying different voltages to the reflecting electrode, the focusing electrode, and the inlet port of the ion introduction section, so as to create electric fields that cause ions in the spray flow passing between the reflecting electrode and the focusing electrode to flow toward the focusing electrode and to flow from the focusing electrode toward the inlet port of the ion introduction section.

In the mass spectrometer according to the present invention, the voltage supplier applies voltages of different values to the reflecting electrode, the focusing electrode, and the inlet port of the ion introduction section, while any one of the voltages may be 0 V. In a case where a certain portion is supplied with a voltage of 0 V, the portion is normally grounded. Accordingly, in a case where any one of the reflecting electrode, the focusing electrode, and the inlet port of the ion introduction section is given a potential of 0 V, the portion is not supplied with a voltage of 0 V from the voltage supplier, but may be simply grounded.

In the mass spectrometer according to the present invention, for example, the ion source is an ESI, APCI or APPI ion source. If the ion source is an ESI ion source, a predetermined level of high direct-current voltage for electrically charging the liquid sample is applied to the tip portion of the ionization probe. If the ion source is an APCI ion source, a discharge electrode for inducing corona discharge for generating buffer ions is provided within or in the vicinity of the space between the ionization probe and the auxiliary electrode. If the ion source is an APPI ion source, a light source for irradiating, with ultraviolet or other kinds of light, the spray flow passing through the space between the point of ejection from the ionization probe and the auxiliary electrode is provided.

In the mass spectrometer according to the present invention, when the measurement target ion is a positive ion, for example, the ion introduction section may be given a ground potential (0 V), and the voltage supplier may apply a predetermined voltage V1 higher than 0 V to the reflecting electrode and may apply a predetermined voltage V2 higher than 0 V but lower than the voltage V1 to the focusing electrode. In other words, the voltages V1 and V2, both satisfying a relationship of V1>V2>0, may be respectively applied to the reflecting electrode and the focusing electrode. The auxiliary electrode may also be given the a ground potential.

Due to a potential difference between the potential of the reflecting electrode and the potentials of the focusing electrode and the inlet port of the ion introduction section (V1−V2, V1), a reflecting electric field, having a force which pushes electrically charged particles, such as ions and electrically charged droplets, in a direction orthogonal or oblique to the flowing direction of the spray flow from the ionization probe, is created within the space between the reflecting electrode and each of the focusing electrode and the ion introduction section, i.e., within the space through which the spray flow passes. Due to the effect of the reflecting electric field, the electrically charged particles traveling in approximately the same direction as the spray flow are deflected to be separated from the gas stream. The reflecting electrode is arranged opposing the focus electrode and the ion introduction section, whereby the force pushing the electrically charged particles in the direction orthogonal to the gas stream is strong. Therefore, the electrically charged particles quickly deviate from an area near the central axis of the spray flow where the gas stream is particularly powerful, and are thus less likely to be affected by the gas stream.

On the other hand, a focusing electric field having a force which pushes the electrically charged particles in a direction to collect them from an area surrounding the space into the ion introduction section is created within the space between the focusing electrode and the ion introduction section. As noted earlier, therefore, as the electrically charged particles approach the focusing electrode due to the reflecting electric field, the effect of the focusing electric field increases so that the electrically charged particles separated from the gas stream can be efficiently collected to the area near the inlet port of the ion introduction section. In this configuration, in the mass spectrometer according to the present invention, even when the spray flow is powerful, ions generated and electrically charged droplets can be efficiently introduced into the inlet port of the ion introduction section and sent through the ion introduction section into the vacuum chamber.

In a preferable aspect of the mass spectrometer according to the present invention, the spraying direction of the liquid sample from the ionization probe extends orthogonally to the direction of introducing the ions by the ion introduction section, the focusing electrode is an electrode of a flat plate shape, having an opening portion into which the ion introduction section is inserted, and extending parallel to a plane orthogonal to a central axis of the inlet port of the ion introduction section, and the reflecting electrode is an electrode of a flat plate shape, extending parallel to the focusing electrode or an electrode of a partially cylindrical shape, extending concentrically with a straight line parallel to a central axis of the spray flow.

The moving speed of an ion within the ionization chamber, in which both the gas stream and the electric field are present in an ambience of substantially atmospheric pressure, depends on a mobility of the ion. The ion mobility in turn depends on the mass, valence, collision cross-section with neutral particles (e.g., residual gas molecules) and other properties of the ion. Therefore, from the viewpoint of the efficiency for an ion to successfully reach the inlet port of the ion introduction section, the optimum strengths of the reflecting electric field and the focusing electric field change depending on the mass-to-charge ratio of the ion. In other words, changing the strengths of the reflecting electric field and the focusing electric field by applying a different voltage to each of the electrodes results in a change in the mass-to-charge ratio of the ion which efficiently reaches the inlet port of the ion introduction section.

Accordingly, in the mass spectrometer according to the present invention, the voltage supplier may preferably be configured to change the applied voltage to at least one of the reflecting electrode, the focusing electrode, and the inlet port of the ion introduction section according to the mass-to-charge ratio of the measurement target ion.

For example, in the case of performing a scan measurement over a predetermined range of mass-to-charge ratios using a quadrupole mass filter as the mass separator, it is preferable to continuously change the applied voltage to any one of the reflecting electrode, focusing electrode, and the inlet port of the ion introduction section synchronously with the operation of continuously changing the applied voltage to the quadrupole mass filter during the scan measurement.

In this configuration, the efficiency of introducing the ions from the ionization chamber into the vacuum chamber can be improved for any mass-to-charge ratio of the measurement target ion.

As noted earlier, changing the strengths of the reflecting electric field and the focusing electric field by applying a different voltage to at least any one of the reflecting electrode, the focusing electrode, and the inlet port of the ion introduction section results in a change in the mass-to-charge ratio of the ion which efficiently reaches the inlet port of the ion introduction section. This means that it is possible to realize a function which corresponds to a differential mobility analyzer (DMA) for separating electrically charged particles according to their electrical mobilities.

In other words, the ion detection device according to the present invention includes:

a) an ionization probe for spraying a liquid sample into an ambience of atmospheric pressure;

b) an ion detection electrode for detecting ions generated from a spray flow from the ionization probe, the ion detection electrode being arranged anterior to the spray flow;

c) a focusing electrode arranged to surround the ion detection electrode without being in contact with the ion detection electrode;

d) a reflecting electrode arranged at a position opposing the ion detection electrode and the focusing electrode across the spray flow from the ionization probe;

e) an auxiliary electrode for shielding an electric field, the auxiliary electrode being arranged between the ionization probe and each of the reflecting electrode and the focusing electrode, the auxiliary electrode having an opening portion through which droplets sprayed from the ionization probe and ions generated from the droplets are passable; and f) a voltage supplier for applying different voltages to the reflecting electrode, the focusing electrode, and the ion detection electrode, so as to create electric fields that cause ions in the spray flow passing between the reflecting electrode and the focusing electrode to flow toward the focusing electrode and to flow from the focusing electrode toward the ion detection electrode.

In the ion detection device according to the present invention, for example, the auxiliary electrode and the inlet port of the ion introduction section are grounded, and the voltage supplier, while maintaining the constant applied voltage to the focusing electrode, changes the applied voltage to the reflecting electrode according to a predetermined sequence. This operation induces a temporal change in the strength of the reflecting electric field within the space between the reflecting electrode and the focusing electrode, and this change in turn causes a change in the ion mobility of the ion which can most efficiently reach the ion detection electrode. Accordingly, it is possible to obtain an ion mobility spectrum which roughly shows a relationship between the ion mobility and an ion intensity, based on the detection signals reflecting the amount of ions (electrically charged particles) which reach the ion detection electrode. Alternatively, the voltages applied from the voltage supplier to the reflecting electrode and the focusing electrode may be fixed at a predetermined level to selectively detect an ion having a specific ion mobility, in which case, for example, a chromatogram showing a temporal change in the intensity of that ion can be obtained.

Advantageous Effects of Invention

In the mass spectrometer according to the present invention, ions generated within an ionization chamber in which an ambience of atmospheric pressure is present can be efficiently collected and introduced through an ion introduction section into a vacuum chamber. More particularly, even when a spray flow ejected from an ionization probe is powerful, ions generated within the spray flow and electrically charged droplets can be efficiently collected and sent into the ion introduction section with minimum waste of the ions and the electrically charged droplets. The amount of ions subjected to mass spectrometry is thereby increased more than in a conventional case, and the sensitivity of the analysis is improved.

The ion detection device according to the present invention has a simple configuration yet can provide an ion mobility spectrum or other forms of information. Thus, it is possible to create an ion mobility spectrometer with a smaller size, lighter weight, lower production cost and other favorable characteristics.

DESCRIPTION OF EMBODIMENTS

Figure 1:
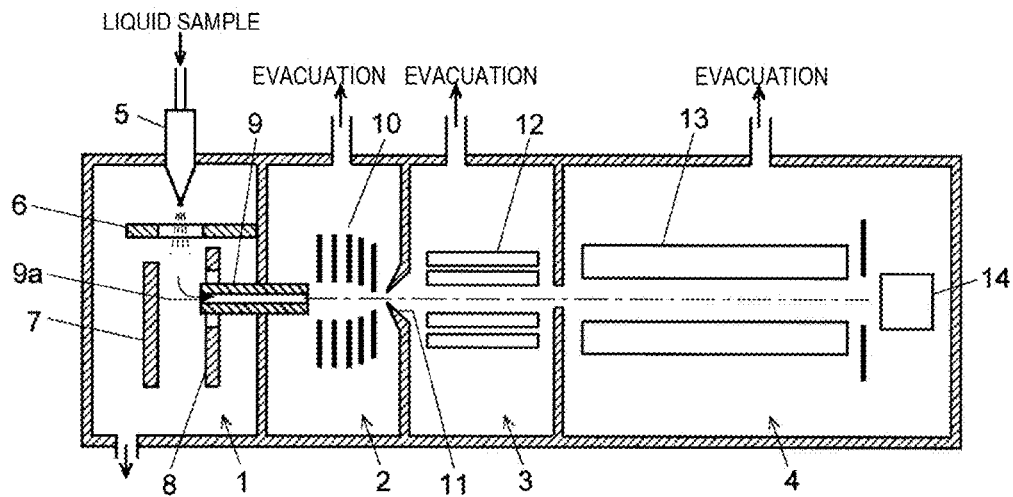
FIG. 1 is a schematic configuration diagram of a mass spectrometer as a first embodiment of the present invention.
Figure 2:
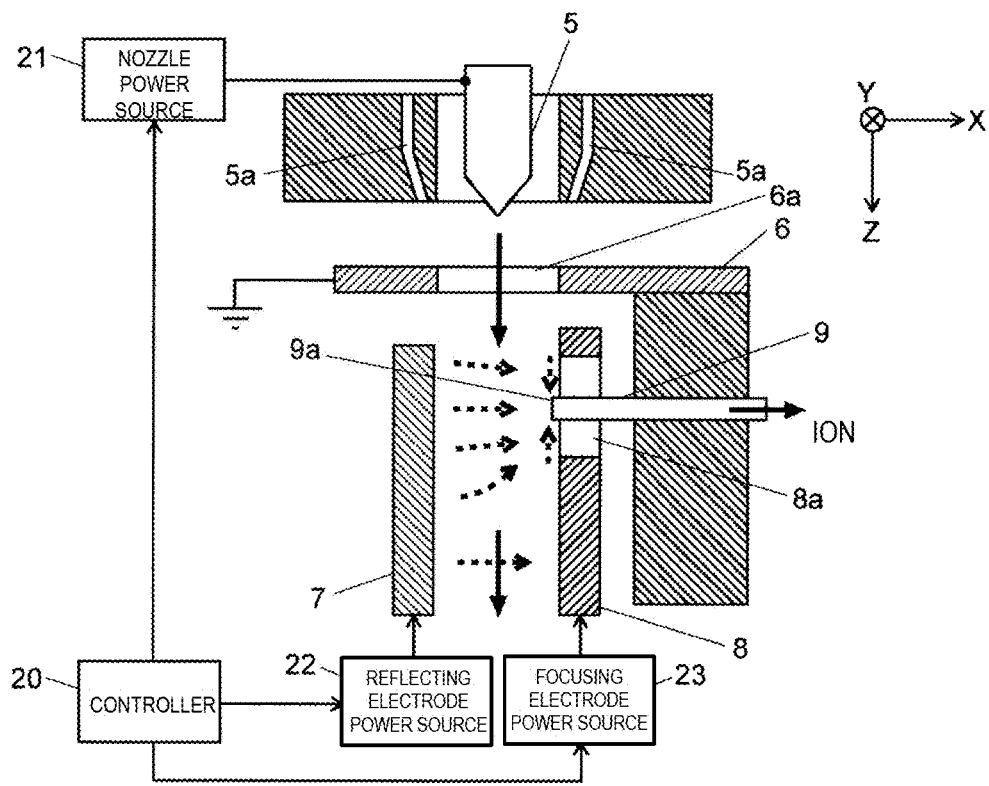
FIG. 2 is a schematic configuration diagram of an ion source in the mass spectrometer of the first embodiment.

A mass spectrometer which is one embodiment (first embodiment) of the present invention is hereinafter described with reference to the accompanying drawings. FIG. 1 is a schematic overall configuration diagram of the mass spectrometer of the first embodiment. FIG. 2 is a schematic configuration diagram of an ion source in the same mass spectrometer.

In FIG. 1, the ambience within an ionization chamber 1 is maintained at substantially atmospheric pressure, while the ambience within an analysis chamber 4 is maintained at a high degree of vacuum by evacuation with a high-performance vacuum pump (not shown). Provided between the ionization chamber 1 and the analysis chamber 4 are a first intermediate vacuum chamber 2 and a second intermediate vacuum chamber 3. In other words, this mass spectrometer has the configuration of a multi-stage differential pumping system with the degree of vacuum increased in a stepwise manner from the ionization chamber 1 in the travelling direction of the ions.

Into the ionization chamber 1, a liquid sample which contains sample components is sprayed from an ESI ionization probe 5 while receiving an imbalanced polarity of electric charges. When the flow rate of the liquid sample is high, heated nebulizer gas may be ejected from a nebulizer-gas tube (see 5a in FIG. 2) concentrically surrounding the sample-spraying nozzle to assist the spraying of the liquid sample. The electrically charged droplets sprayed from the tip of the ionization probe 5 are broken into finer droplets by coming into contact with the ambient gas, with the solvent vaporizing from those droplets. During this process, the sample components carrying electric charges are ejected from the droplets, forming ions. An auxiliary electrode 6, a reflecting electrode 7, and a focusing electrode 8, which have respective functions as will be described later, are provided anterior to the spray flow from the ionization probe 5.

The ionization chamber 1 and the first intermediate vacuum chamber 2 communicate with each other through a thin heated capillary 9, which corresponds to the ion introduction section in the present invention. There is a pressure difference between the two open ends of this heated capillary 9, and this pressure difference creates a gas stream flowing from the ionization chamber 1 into the first intermediate vacuum chamber 2 through the heated capillary 9. The ions generated from the sample components within the ionization chamber 1 are carried mainly by this gas stream and drawn into the heated capillary 9, to be ejected from the outlet end of the same capillary into the first intermediate vacuum chamber 2 along with the gas stream. A skimmer 11 having a small orifice at its apex is provided in a partition wall which separates the first intermediate vacuum chamber 2 and the second intermediate vacuum chamber 3. The first intermediate vacuum chamber 2 contains an ion guide 10 composed of multiple plate electrodes arranged around an ion beam axis. Due to the effect of the electric field created by this ion guide 10, the ions introduced into the first intermediate vacuum chamber 2 are converged to the vicinity of the orifice of the skimmer 11, to be sent through the orifice into the second intermediate vacuum chamber 3.

The second intermediate vacuum chamber 3 contains a multipole (e.g., octupole) ion guide 12. Due to the effect of a radiofrequency electric field created by this ion guide 12, the ions are converged and sent into the analysis chamber 4. Within the analysis chamber 4, the ions are introduced into a space extending along the longitudinal axis of a quadrupole mass filter 13. Due to the effect of the electric field created by a radiofrequency voltage and direct-current voltage applied to the quadrupole mass filter 13, only ions having a specific mass-to-charge ratio are allowed to pass through the quadrupole mass filter 13 and reach an ion detector 14. The ion detector 14 produces detection signals corresponding to the amount of ions which have reached the detector 14, and feeds the signals to a data processing unit (not shown). By allowing the measurement target ions among the ions generated from the sample components within the ionization chamber 1 to eventually enter the ion detector 14 with minimum loss of the ions, a high-sensitivity analysis can be realized.

For convenience, as shown in FIG. 2, the spraying direction along the central axis of the spray flow from the ionization probe 5 is referred to as a Z-axis direction, the ion-drawing direction extending orthogonally to the Z-axis direction and along the central axis of the heated capillary 9 is referred to as an X-axis direction, and a direction extending orthogonally to the Z-axis direction and the X-axis direction is referred to as a Y-axis direction.

Within the ionization chamber 1, the auxiliary electrode 6, having a flat plate shape and extending parallel to a plane defined by the X-axis and the Y-axis, is arranged closest to the ionization probe 5. The auxiliary electrode 6 has an opening portion 6a having a circular shape of a predetermined diameter and formed concentrically about the central axis of the spray flow. The heated capillary 9 has an inlet end portion which is surrounded by the focusing electrode 8 having a flat plate shape and extending parallel to a plane defined by the Y-axis and the Z-axis. The focusing electrode 8 has an opening portion 8a formed in a circular shape. The inlet end portion of the heated capillary 9, which is an inlet end 9a, is arranged at a center of the opening portion 8a and slightly protruded into the spray flow from a surface of the focusing electrode 8 facing the spray flow. The inlet end 9a of the heated capillary 9 and the focusing electrode 8 oppose the reflecting electrode 7, having a flat plate shape and extending parallel to the plane defined by the Y-axis and the Z-axis, across the spray flow. In other words, the spray flow is sandwiched between the reflecting electrode 7 and the focusing electrode 8, both extending parallel to each other, and the auxiliary electrode 6 is located between the reflecting electrode 7, the focusing electrode 8, and the ionization probe 5.

The auxiliary electrode 6, and an electrically conductive partition wall which is electrically connected to the heated capillary 9, are grounded, and the respective potentials are 0 V. The reflecting electrode 7 is supplied with a predetermined direct-current voltage V1 from a reflecting electrode power source 22, and the focusing electrode 8 is supplied with a predetermined direct-current voltage V2 from a focusing electrode power source 23. To the ionization probe 5, a high direct-current voltage with a maximum level of approximately several kV is applied from a nozzle power source 21 so that the liquid sample is electrostatic sprayed from the ionization probe 5. The polarity of each of the voltages V1 and V2 respectively applied to the reflecting electrode 7 and the focusing electrode 8 is selected according to the polarity of the measurement target ion. When the measurement target ion is a positive ion, both of the voltages V1 and V2 have the positive polarity. The voltages respectively generated by the nozzle power source 21, the reflecting electrode power source 22, and the focusing electrode power source 23 are controlled by a controller 20.

The following description assumes that the measurement target ion is a positive ion. When the measurement target ion is a negative ion, only the polarity of the applied voltages needs to be changed.

A relationship of V1>V2>V3 is satisfied, where V1 represents the voltage applied to the reflecting electrode 7, V2 represents the voltage applied to the focusing electrode 8, and V3 (which is 0 V in this example) represents the voltage applied to the heated capillary 9. For example, the voltage V1 is 6 kV, the voltage V2 is 4 kV, and the voltage V3 is 0 V.

Due to a high positive voltage applied to the ionization probe 5 from the nozzle power source 21, the liquid sample is positively charged and sprayed. As shown by a thick solid arrow in FIG. 2, the spray flow ejected from the ionization probe 5 travels roughly downward (in the Z-axis direction). Positive polarity ions generated from the sample droplets travel in approximately the same direction. Almost all these ions, along with the gas stream, pass through the opening portion 6a of the auxiliary electrode 6 to travel into the space sandwiched between the reflecting electrode 7 and the focusing electrode 8. The auxiliary electrode 6 is grounded, whereby electric fields in both spaces sandwiching the auxiliary electrode 6 are hardly affected by each other.

As noted earlier, the positive polarity voltages, V1, V2, and V3 satisfy the relationship of V1>V2>V3. Accordingly, a reflecting electric field, having a force which pushes positive ions in a direction from the reflecting electrode 7 toward the focusing electrode 8, is created between the reflecting electrode 7 and the focusing electrode 8. A potential difference between the reflecting electrode 7 and the heated capillary 9 is larger than a potential difference between the reflecting electrode 7 and the focusing electrode 8, whereby a reflecting electric field is further created. The reflecting electric field has a force which pushes the ions more strongly from the reflecting electrode 7 toward the heated capillary 9. Additionally, a focusing electric field is created. The focusing electric field has a force pushing positive ions in a direction from the focusing electrode 8 toward the heated capillary 9, i.e., from an inner edge of the opening portion 8a of the focusing electrode 8 toward a center of the focusing electrode 8.

As noted earlier, the spray flow, including the ions which have passed through the opening portion 6a of the auxiliary electrode 6, travels downward in the space between the reflecting electrode 7 and the focusing electrode 8. However, due to the aforementioned effect of the reflecting electric field, the positively charged ions are pushed toward the focusing electrode 8 to be separated from the gas stream. Particularly in a region where the ions traveling on the spray flow have passed through the inlet end 9a of the heated capillary 9, a force, which pushes back the ions obliquely upward to the inlet end 9a, acts on the ions. Consequently, the gas stream continues to travel downward, whereas the electrically charged particles, such as ions and electrically charged micro-droplets which have not been ionized yet, are separated from the gas stream and are pushed back in the upward direction, to be suspended near the inlet end 9a of the heated capillary 9. Then, due to the effect of the focusing electric field being active between the focusing electrode 8 and the heated capillary 9, the electrically charged particles spreading out are converged to close on the inlet end 9a.

The ions and the electrically charged micro-droplets collected in the vicinity of the inlet end 9a of the heated capillary 9 are drawn into the heated capillary 9 and sent to the first intermediate vacuum chamber 2. While passing through the heated capillary 9, the solvent contained in the electrically charged droplets vaporizes, whereby the ionization continues within the heated capillary 9. Thus, in the mass spectrometer of the present embodiment, a large amount of ions and electrically charged micro-droplets which would be directly carried away by the gas stream and disposed of in a conventional case can be efficiently collected.

Figure 3B:
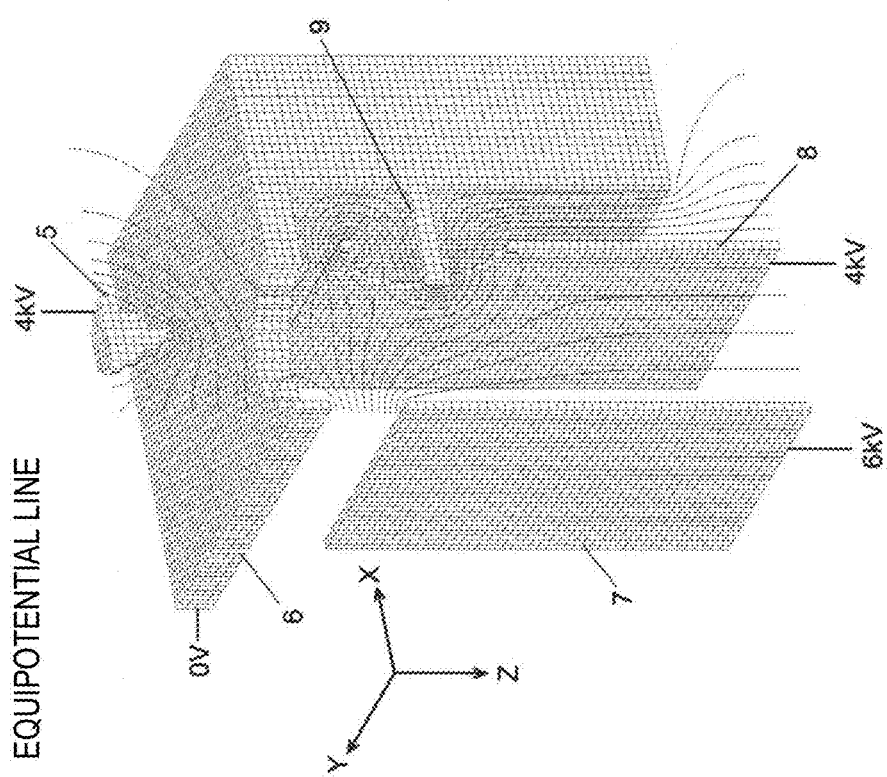
FIGS. 3A and 3B are graphics showing simulation results of an equipotential line and an ion trajectory in the ion source shown in FIG. 2.
Figure 3A:
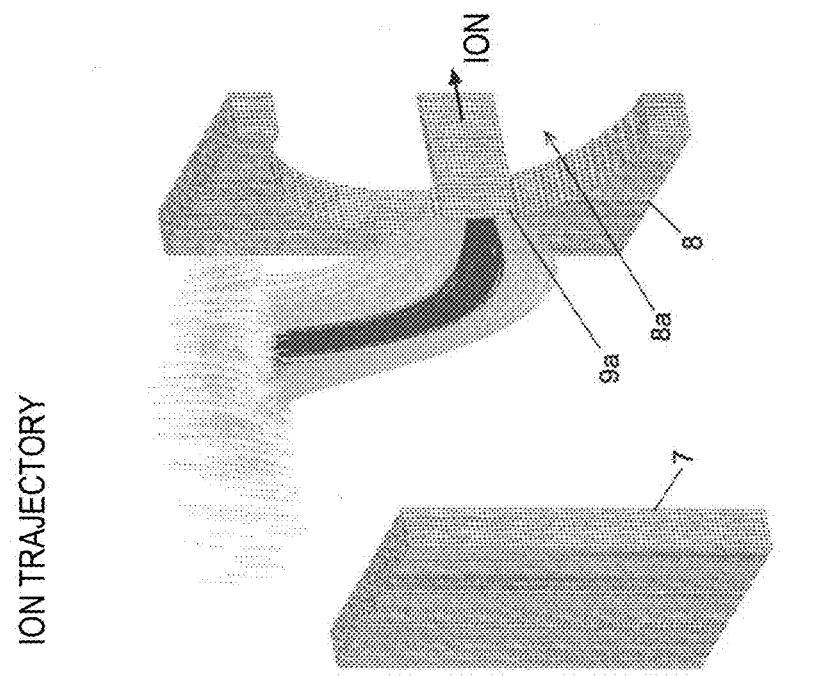

FIGS. 3A and 3B are graphics showing simulation calculation results of an equipotential line and an ion trajectory in the ion source.

FIG. 3A shows equipotential lines on a plane being defined by the X-axis and the Z-axis and including the central axis of the heated capillary 9. The force pushing the ions acts basically in an orthogonal direction to these equipotential lines. The smaller an interval between the equipotential lines is, the more effective the force acting on the ions becomes. As seen from FIG. 3A, in the vicinity of the inlet end 9a of the heated capillary 9, a strong force acts on the ions to drive them toward the inlet end 9a. Due to the effect of such an electric field, as shown in FIG. 3B, almost all the ions are separated from the gas stream and are reflected, to be focused to the inlet end 9a of the heated capillary 9. These results confirm that a large number of ions which would be disposed of in a conventional case are effectively introduced into the first intermediate vacuum chamber 2.

Figure 4A:
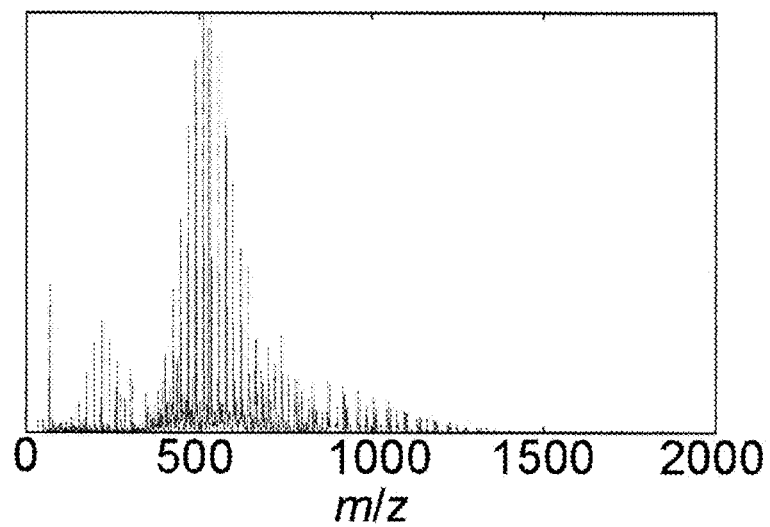
FIG. 4A is a diagram showing a mass spectrum obtained from a conventional mass spectrometer.
Figure 4B:
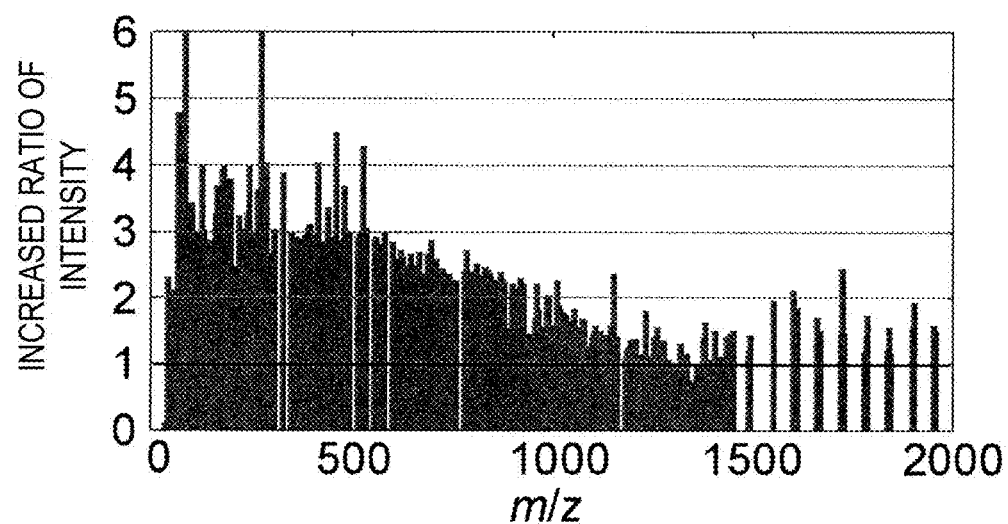
FIG. 4B is a diagram showing, with reference to the mass spectrum shown in FIG. 4A, an increased ratio of each peak signal intensity in a mass spectrum obtained from the mass spectrometer of the first embodiment.

In order to confirm the aforementioned effect of improving the ion collection efficiency, an experiment actually conducted upon a mass spectrometer of the present embodiment is hereinafter described. Based on a mass spectrum obtained from a conventional mass spectrometer which measured a predetermined sample, this experiment examined an increased ratio of each peak signal intensity in a mass spectrum obtained from the mass spectrometer of the present embodiment which measured the same predetermined sample. FIG. 4A shows a reference mass spectrum, and FIG. 4B shows the increased ratio of peak signal intensity. As seen from FIG. 4B, the peak signal intensity increases two to three times over a wide range of m/z values. This result confirms the improved ion collection efficiency in the mass spectrometer of the present embodiment, whereby the peak signal intensity is reliably improved.

In the mass spectrometer of the present embodiment, the efficiency of collecting the ions to the inlet end 9a of the heated capillary 9 depends on the strength of the electric field within the space between the reflecting electrode 7 and the focusing electrode 8, the shape of the equipotential lines, and the mass-to-charge ratio of the ion. Therefore, in order to improve the sensitivity of the analysis, it is effective to change the voltages V1 and V2 applied respectively to the reflecting electrode 7 and the focusing electrode 8, according to the mass-to-charge ratio of the measurement target ion, more specifically, the ion to be selected by the quadrupole mass filter 13.

Accordingly, in the mass spectrometer of the present embodiment, for example, the optimum voltages V1 and V2 are experimentally determined beforehand for each of the mass-to-charge ratios of the measurement target ions, and a calculation formula or table showing a relationship between the mass-to-charge ratio and each of the optimum voltages V1 and V2 is created and stored in the controller 20. When an analysis of a target sample is performed, the controller 20 determines, based on the aforementioned calculation formula or table, each of the optimum voltages V1 and V2 according to the voltage applied to the quadrupole mass filter 13 (i.e., according to the mass-to-charge ratio of the ion to be selected by the quadrupole mass filter 13) so as to control the reflecting electrode power source 22 and the focusing electrode power source 23. Accordingly, the voltages applied respectively to the reflecting electrode 7 and the focusing electrode 8 become equal to the optimum voltages V1 and V2. In the case where the voltage applied to the quadrupole mass filter 13 is continuously changed to perform a scan measurement over a predetermined range of mass-to-charge ratios, each of the voltages V1 and V2 is also changed synchronously with the scan operation. As a result, ions are introduced into the first intermediate vacuum chamber 2 and subsequent sections with high efficiency over the entire range of mass-to-charge ratios.

The ion mobility depends on the mass-to-charge ratio of the ion, and as noted earlier, changing the voltages V1 and V2 results in a change in the mass-to-charge ratio of the ion to be efficiently introduced into the heated capillary 9. Thus, in order to constantly achieve a high efficiency of collecting the measurement target ions, instead of synchronously changing the voltages V1 and V2 with the voltage applied to the quadrupole mass filter 13, it is possible to use the auxiliary electrode 6, the reflecting electrode 7, the focusing electrode 8, and the heated capillary 9 as an ion mobility spectrometry unit for changing the mobility of an ion to be monitored, or it is possible to use them as an ion mobility filter for selecting ions having a specific mobility.

For example, the intensities of various ions which have a specific mass-to-charge ratio yet differ from each other in ion mobility can be determined by continuously changing at least one of the voltages V1 and V2 as appropriate, with the mass-to-charge ratio of the ion to be selected by the quadrupole mass filter 13 fixed. It is also possible to fix each of the voltages V1 and V2 and change the mass-to-charge ratio of the ion to be selected by the quadrupole mass filter 13 over a predetermined range of mass-to-charge ratios, so as to investigate a relationship between the mass-to-charge ratio and an ion intensity for ions having a specific ion mobility.

Figure 5:
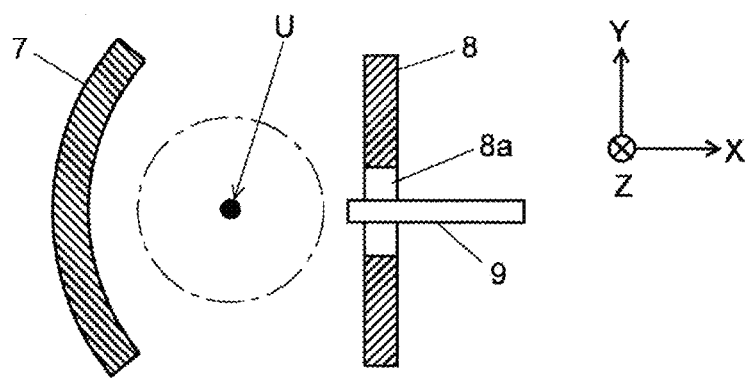
FIG. 5 is a schematic configuration diagram of an ion source in a mass spectrometer as a modification of the present invention.

In the mass spectrometer of the first embodiment, the auxiliary electrode 6, the reflecting electrode 7, and the focusing electrode 8 each have a flat plate shape. Alternatively, it is possible to modify the shape of these electrodes. FIG. 5 shows an example in the case where the reflecting electrode 7 has a partially cylindrical shape (cylindrical shape taken along a plane parallel to the plane including the central axis of the cylindrical body). In FIG. 5, the Z-axis direction extends orthogonally, and U represents the central axis of the spray flow. By applying such a shape to the reflecting electrode 7, the force acting on the ions due to the electric field within the space between the reflecting electrode 7 and the focusing electrode 8 causes the ions to further flow in the direction toward the inlet end 9a. Consequently, it is possible to further improve the efficiency of collecting ions.

Figure 6:
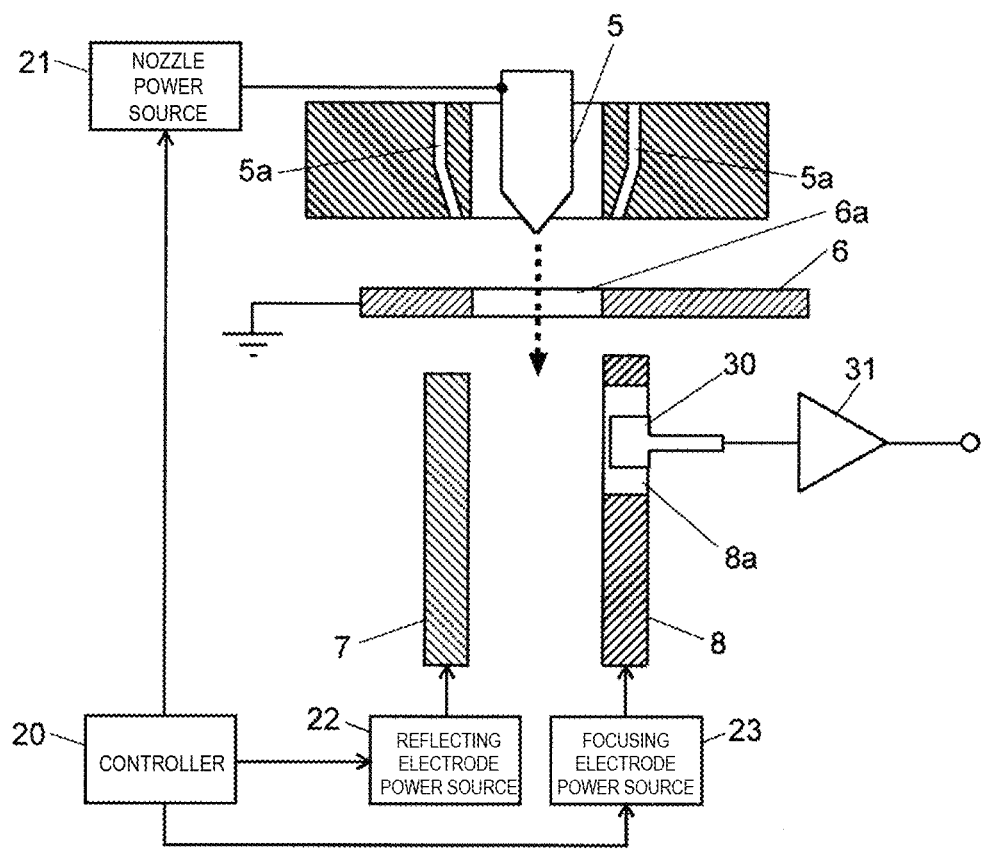
FIG. 6 is a schematic configuration diagram of an ion detection device as a second embodiment of the present invention.

An ion detection device which is another embodiment (second embodiment) of the present invention is hereinafter described. FIG. 6 is a schematic configuration diagram of the ion detection device of the second embodiment.

As noted earlier, in the configuration shown in FIG. 2, a change in each of the voltages V1 and V2 causes a change in the efficiency for an ion having a specific mass-to-charge ratio to reach the inlet end 9a of the heated capillary 9. That is to say, the efficiency of collecting ions to the inlet end 9a of the heated capillary 9 has a dependency on the ion mobility. Making use of this fact, the ion detection device of the present embodiment separates and detects ions according to the ion mobility.

In the ion detection device of the present embodiment, an ion detection electrode 30 is provided at the location where the inlet end 9a of the heated capillary 9 was located in the mass spectrometer of the first embodiment. An ion current obtained with the ion detection electrode 30 is amplified by an amplifier 31 and provided as a detection signal. When an ion mobility spectrum showing a relationship between the ion mobility and the ion intensity needs to be obtained, the controller 20 operates the reflecting electrode power source 22 and the focusing electrode power source 23 so that one of or each of the voltages V1 and V2 is continuously changed over a predetermined range. With this operation, the mobility of the ion which can most efficiently reach the ion detection electrode 30 also changes. Therefore, an ion mobility spectrum can be created based on the detection signal by the ion detection electrode 30. When a temporal change in the ion intensity of the ions having a specific ion mobility needs to be monitored, the controller 20 operates the reflecting electrode power source 22 and the focusing electrode power source 23 so that the voltage(s) V1 and/or V2 corresponding to the ion mobility of the ion is applied to the reflecting electrode 7 and/or the focusing electrode 8. By this operation, the state in which the ions having that specific ion mobility can most efficiently reach the ion detection electrode 30 is maintained. Therefore, a chromatogram for ions having that specific ion mobility can be created based on the detection signal.

Conventional ion detection devices making use of the ion mobility can separate ions with high resolving power according to the ion mobility. However, those systems are large in scale due to such factors as a complex electrode configuration for creating electric fields as well as a complex structure for generating a gas flow with a constant flow velocity. By comparison, in the ion detection device of the present embodiment, the section for separating ions according to their mobility has an extremely simple configuration and allows for the realization of a small and inexpensive device. Therefore, for example, a system which is suitable as an option for a detector for liquid chromatographs can be provided. The shape of each electrode can be appropriately modified, for example, the reflecting electrode 7 shaped as in FIG. 5 may be also used in the configuration of FIG. 6.

It should be noted that any of the previous embodiments is a mere example of the present invention, and any change, modification or addition appropriately made within the spirit of the present invention will naturally fall within the scope of claims of the present application.

REFERENCE SIGNS LIST

1 . . . Ionization Chamber
2 . . . First Intermediate Vacuum Chamber
3 . . . Second Intermediate Vacuum Chamber
4 . . . Analysis Chamber
5 . . . Ionization Probe
6 . . . Auxiliary Electrode
6a . . . Opening portion
7 . . . Reflecting Electrode
8 . . . Focusing Electrode
8a . . . Opening portion
9 . . . Heated Capillary
9a . . . Inlet End
10 . . . Ion Guide
11 . . . Skimmer
12 . . . Ion Guide
13 . . . Quadrupole Mass Filter
14 . . . Ion Detector
20 . . . Controller
21 . . . Nozzle Power Source
22 . . . Reflecting Electrode Power Source
23 . . . Focusing Electrode Power Source
30 . . . Ion Detection Electrode
31 . . . Amplifier

The invention claimed is:

1. A mass spectrometer provided with: an ion source including an ionization probe for spraying a liquid sample into an ionization chamber in which an ambience of atmospheric pressure is present; and an ion introduction section for sending, from the ionization chamber to a vacuum chamber, ions generated by the ion source from a component contained in sample droplets sprayed from the ionization probe, where the arrangement of the ionization probe and the ion introduction section is determined so that the spraying direction of the liquid sample from the ionization probe extends orthogonally or obliquely to the direction of introducing the ions from the ionization chamber by the ion introduction section,
the mass spectrometer comprising:
a) a focusing electrode arranged to surround an inlet port of the ion introduction section, without being in contact with the ion introduction section;
b) a reflecting electrode arranged at a position opposing the inlet port of the ion introduction section and the focusing electrode across the spray flow of sample droplets ejected from the ionization probe;
c) an auxiliary electrode for shielding an electric field, the auxiliary electrode being arranged between the ionization probe and each of the reflecting electrode and the focusing electrode, the auxiliary electrode having an opening portion through which the droplets sprayed from the ionization probe and ions generated from the droplets are passable; and
d) a voltage supplier for applying different voltages to the reflecting electrode, the focusing electrode, and the inlet port of the ion introduction section, so as to create electric fields that cause ions in the spray flow passing between the reflecting electrode and the focusing electrode to flow toward the focusing electrode and to flow from the focusing electrode toward the inlet port of the ion introduction section.

2. The mass spectrometer according to claim 1, wherein the spraying direction of the liquid sample from the ionization probe extends orthogonally to the direction of introducing the ions by the ion introduction section, the focusing electrode is an electrode of a flat plate shape, having an opening portion into which the ion introduction section is inserted, and extending parallel to a plane orthogonal to a central axis of the inlet port of the ion introduction section, and
the reflecting electrode is an electrode of a flat plate shape, extending parallel to the focusing electrode or an electrode of a partially cylindrical shape, extending concentrically with a straight line parallel to a central axis of the spray flow.

3. The mass spectrometer according to claim 1, wherein the voltage supplier is configured to change voltages to be applied to at least one of the reflecting electrode, the focusing electrode, and the inlet port of the ion introduction section according to mass-to-charge ratio of a measurement target ion.

4. The mass spectrometer according to claim 1, wherein the ion source employs an electrospray ionization method.

5. The mass spectrometer according to claim 1, wherein the ion source employs an atmospheric pressure chemical ionization method.

6. The mass spectrometer according to claim 1, wherein the ion source employs an atmospheric pressure photoionization method.

7. An ion detection device comprising:
a) an ionization probe for spraying a liquid sample into an ambience of atmospheric pressure;
b) an ion detection electrode for detecting ions generated from a spray flow from the ionization probe, the ion detection electrode being arranged anterior to the spray flow;
c) a focusing electrode arranged to surround the ion detection electrode without being in contact with the ion detection electrode;
d) a reflecting electrode arranged at a position opposing the ion detection electrode and the focusing electrode across the spray flow from the ionization probe;
e) an auxiliary electrode for shielding an electric field, the auxiliary electrode being arranged between the ionization probe and each of the reflecting electrode and the focusing electrode, the auxiliary electrode having an opening portion through which droplets sprayed from the ionization probe and ions generated from the droplets are passable; and
f) a voltage supplier for applying different voltages to the reflecting electrode, the focusing electrode, and the ion detection electrode, so as to create electric fields that cause ions in the spray flow passing between the reflecting electrode and the focusing electrode to flow toward the focusing electrode and to flow from the focusing electrode toward the ion detection electrode.

* * * * *